(12) United States Patent
Kempen

(10) Patent No.: US 6,594,011 B1
(45) Date of Patent: Jul. 15, 2003

(54) IMAGING APPARATUS AND METHOD

(75) Inventor: Lothar U. Kempen, Redondo Beach, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 201 days.

(21) Appl. No.: 09/614,503

(22) Filed: Jul. 11, 2000

(51) Int. Cl.$^7$ .......................... G01J 4/00; G01N 33/557
(52) U.S. Cl. ...................... 356/369; 356/445; 436/517; 436/805
(58) Field of Search ................................. 356/364–369, 356/445, 446, 128, 136; 422/82.08, 82, 11; 435/6, 7.1, 808, 288.7; 436/517, 805, 527

(56) References Cited

U.S. PATENT DOCUMENTS

| 4,508,832 A |   | 4/1985 | Carter et al. ................. 436/517 |
| 5,229,833 A | * | 7/1993 | Stewart ........................ 356/364 |
| 5,255,075 A | * | 10/1993 | Cush ........................... 356/445 |
| 5,437,840 A |   | 8/1995 | King et al. ............... 422/82.08 |
| 5,483,346 A |   | 1/1996 | Butzer ......................... 356/369 |
| 5,485,277 A | * | 1/1996 | Foster ......................... 356/445 |
| 5,491,556 A | * | 2/1996 | Stewart et al. ............... 356/445 |
| 5,633,724 A |   | 5/1997 | King et al. .................. 356/445 |
| 5,856,873 A | * | 1/1999 | Naya et al. .................. 356/369 |

OTHER PUBLICATIONS

"Optical Characterization of Very Thin Hydrogenated Amorphous Silicon Films Using Spectroscopic Ellipsometry"; by Saitoh; Hori; Suzuki; & Iida; Japanese Journal of Applied Physics; 1991.
"Handbook of Optics", by The Optical Society of America; vol. 1; pp. 4.23, 4.24; 1995.
"Imaging Ellipsometry Revisited: Developments for Visualization of Thin Transparent Layers on Silicon Substrates", by Gang Jin, et al., Rev. Sci. Instrum., pp. 2930–2936, 1996.
"Principles of Optics—Electromagnetic Theory of Propagation, Interference and Diffraction of Light", by Max Born & Emil Wolf, Sixth Edition, pp. 47–51.
"Biosensors: An Introduction", by Brian R. Eggins, pp. 112–113, 1987.
"Monitoring Specific Interaction of Low Molecular Weight Biomolecules on Oxidized Porous Silicon Using Ellipsometry", byD. Van Noort; S. Welin–Klintstrom, et al., Biosensors & Bioelectronics vol. 13, pp. 439–449, 1997.
"Imaging Ellipsometry for Biosensor Applications", by Gang Jin, et al., Transducers '95.Eurosensors IX, pp. 509–774, 1995.
"Waveguide Ellipsometry Biosensors: Concept and Preliminary Analysis", SPIE vol. 1648, by Jinyu Wang, pp. 44–50, 1992.
"Flow–Injection Ellipsometry—An in Situ Method for the Study of Biomolecular Adsorption and Interaction at Solid Surfaces", by Ulf Jonsson, et al., Colloids and Surfaces, pp. 333–339, 1985.
"Biosensors Based on Surface Concentration Measuring Devices—The Concept of Surface Concentration", by Ulf Jonsson, et al., Progress in Colloid and Polymer Sci. 70, pp. 96–100, 1985.

(List continued on next page.)

Primary Examiner—Hoa Q. Pham
(74) Attorney, Agent, or Firm—Lawrence S. Cohen

(57) ABSTRACT

Imaging apparatus and method which uses change of polarization state of a light beam passed through a total internal reflection structure by a single reflection at a TIR surface in which a specimen is placed in the evanescent field associated with the total internal reflection of the light beam, the specimen being the subject of biological, chemical or genetic investigation.

32 Claims, 2 Drawing Sheets

OTHER PUBLICATIONS

"[34] Surface Immobilization Techniques in Combination with Ellipsometry", by Ulf Jonsson, et al., Methods in Enzymology, vol. 137, pp. 381–1351, 1988.

"Characterization of Biomembranes by Spectral Ellipsometry, Surface Plasmon Resonance and Interferometry with Regard to Biosensor Application", by Ch. Striebel, et al., Biosensors & Bioelectronics 9, pp. 139–146, 1994.

"Ellipsometric Immunosensors for the Determination of Y–Interferon and Human Serum Albumin", by T.A. Ruzgas, et al., Biosensors & Bioelectronics 7, pp. 305–308, 1992.

"Determination by Ellipsometry of the Affinity of Monoclonal Antibodies", by Haken Nygren, et al., Journal of Immunological Methods, 92, pp. 219–221, 1986.

"Opto–Electronic Immunosensors: A Review of Optical Immunoassay at Continuous Surfaces", by John F. Place, et al., Biosensors 1, pp. 321–353, 1985.

Biosensors: Fundamental, Technologies and Applications, by A. Brecht, et al., edited by F. Scheller, et al., GBF Monographs vol. 17, pp. 174–178, 1991.

"Kinetics of Antibody–Binding to Surface–Immobilized Antigen: Influence of Mass Transport on the Enzyme–Linked Immunosorbent Assay (Elisa)", by Nygren & Stenberg, Journal of Colloid and Interface Science, vol. 107, pp. 560–566, 1985.

"Effects of Hydrophilization and Immobilization on the Interfacial Behavior of Immunoglobulins", by Martin Malmsten, et al., Journal of Colloid and Interface Science 177, pp. 70–78, 1994.

"Temporal Studies on the Deposition of Complement on Human Colostrum IgA and Serum IgG Immobilized on Methylated Silicon", by Pentti Tengvall, et al., Journal of Biomedical Materials Research, vol. 35, pp. 81–91, 1997.

"Assembly of Antibodies in Lipid Membranes for Biosensor Development", by Huaiyou Wang, et al., Applied Biochemistry and Biotechnology, pp. 163–181, 1994.

"Wetting and Dewetting of Si/SiO2–Wafers by Free and Lipid–Monolayer Covered Aqueous Solutions Under Controlled Humidity", by G. Elender, et al., Journal de Physique II, pp. 455–479, 1994.

"Coupling of Biomolecules to Silicon Surfaces for Use in Ellipsometry and Other Related Techniques", by Carl Fredrik Mandenius, et al., Methods in Enzymology, vol. 137, pp. 388–394, 1988.

"Patterning of Immobilized Antibody Layers via Photolithography and Oxygen Plasma Exposure", by A.W. Flounders, et al., Biosensors and Bioelectronics vol. 12, pp. 447–456, 1997.

"A Comparative Study of Protein Immobilization Techniques for Optical Immunosensors", by A. Ahluwalia, et al., Biosensors and Bioelectronics 7, pp. 207–214, 1991.

"Universal Imaging Corporation—Metapolscope"; "Metamorph Imaging System", by Dr. Rudolf Oldenbourg, pp. 1–2.

"A New View on Polarization Microscopy", by Rudolf Oldenbourg, Nature vol. 381, pp. 811–812, Jun. 27, 1996.

"Structural Analysis with Quantitative Birefringence Imaging", by Clifford C. Hoyt, et al., American Laborary, pp. 34–42, Jul. 1999.

"Direct Visualization of Monolayers at the Air–Water Interface by Brewster Angle Microscopy", by Dirk Honig, et al., J. Phys. Chem., pp. 4590 & 4592, 1991.

"Microscope at the Brewster Angle: Direct Observation of First–Order Phase Transitions in Monolayers", by S. Henon, et al., Rev. Sci. Instrum. 62, pp. 936–939, 1990.

"A Biosensor Concept Based on Imaging Ellipsometry for Visualization of Biomolecular Interactions", by Gang Jin, et al., Analytical Biochemistry 232, pp. 69–72, 1995.

"Complement Activation by 3–Mercapto–1,2–Propanediol Immobilized on Gold Surfaces", by Pentti Tengvall, et al., Biomaterials 17, pp. 1001–1007, 1995.

"Spectroscopic Ellipsometry and Biology: Recent Developments and Challenges", by H. Arwin, Thin Solid Films 313–314, pp. 764–774, 1998.

* cited by examiner

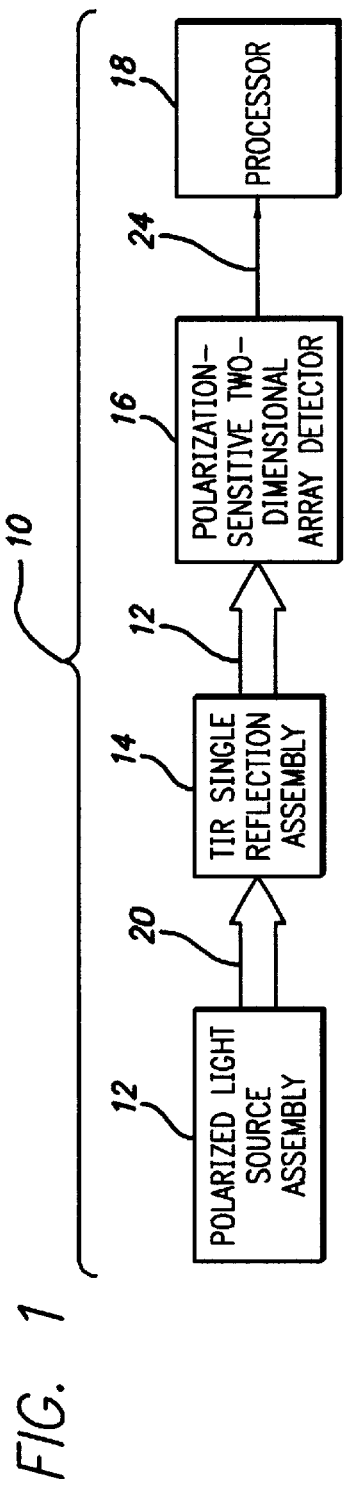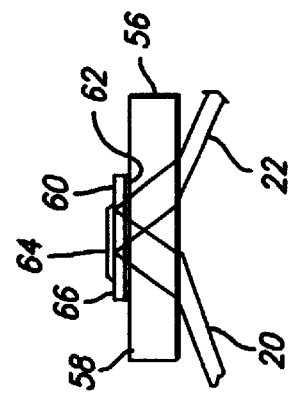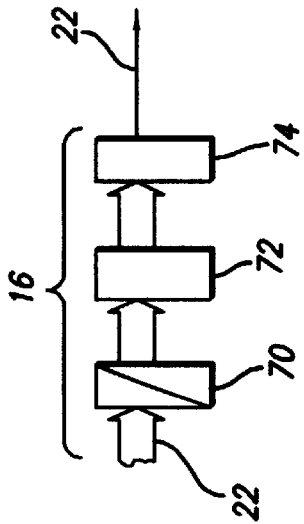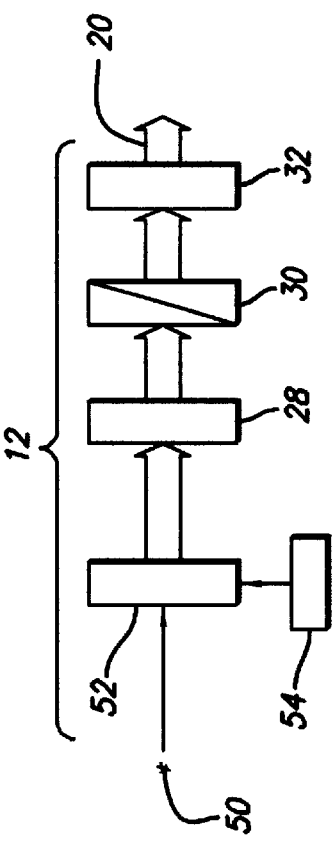

IMAGING APPARATUS AND METHOD

FIELD OF THE INVENTION

This invention relates to imaging techniques in conjunction with total internal reflection at the boundary of an optically transparent material and more particularly to the use of such techniques for detecting the presence, composition, quantity, and spatial distribution of substances on optically transparent substrates.

BACKGROUND OF THE INVENTION

It is well known that the presence or the properties of substances on a material's surface can be determined by light-based sensors. Polarization-based techniques are particularly sensitive; ellipsometry, for example, is a widely used technique for surface analysis and has successfully been employed for detecting attachment of proteins and smaller molecules to a surface. In U.S. Pat. No. 4,508,832 to Carter, et al. (1985), an ellipsometer is employed to measure antibody-antigen attachment in an immunoassay on a test surface. Recently, imaging ellipsometry has been demonstrated, using a light source to illuminate an entire surface and employing a two-dimensional array for detection, thus measuring the surface properties for each point of the entire surface in parallel(G. Jin, R. Janson and H. Arwin, "Imaging Ellipsometry Revisited: Developments for Visualization of Thin Transparent Layers on Silicon Substrates," Review of Scientific Instruments, 67(8), 2930–2936, 1996). Imaging methods are advantageous in contrast to methods performing multiple single-point measurements using a scanning method, because the status of each point of the surface is acquired simultaneously, whereas the scanning process takes a considerable amount of time (for example, some minutes), and creates a time lag between individual point measurements. For performing measurements where dynamic changes of the surface properties occur in different locations, a time lag between measurements makes it difficult or impossible to acquire the status of the entire surface at any given time. Reported applications of imaging ellipsometry were performed on a silicon surface, with the light employed for the measurement passing through +the surrounding medium, either air or a liquid contained in a cuvette. For applications where the optical properties of the surrounding medium can change during the measurement process, passing light through the medium is disadvantageous because it introduces a disturbance of the measurement.

By using an optically transparent substrate, this problem can be overcome using the principle of total internal reflection (TIR), where both the illuminating light and the reflected light pass through the substrate. In TIR, the light interacting with the substance on the surface is confined to a very thin region above the surface, the so-called evanescent field. This provides a very high contrast readout, because influences of the surrounding medium are considerably reduced. In U.S. Pat. No. 5,483,346 to Butzer, (1996) the use of polarization for detecting and analyzing substances on a transparent material's surface using TIR is described. In the system described by Butzer, however, the light undergoes multiple internal reflections before being analyzed, making it difficult or impossible to perform an imaging technique, because it cannot distinguish which of the multiple reflections caused the local polarization change detected in the respective parts of the emerging light beam. U.S. Pat. No. 5,633,724 to King, et al. (1997) describes the readout of a biochemical array using the evanescent field. This patent focuses on fluorescent assays, using the evanescent field to excite fluorescent markers attached to the substances to be detected and analyzed. The attachment of fluorescent markers or other molecular tags to the substances to be detected on the surface requires an additional step in performing the measurement, which is not required in the current invention. The patent further describes use of a resonant cavity to provide on an evanescent field for exciting analytes.

SUMMARY OF THE INVENTION

In accordance with the principles of this invention, light from a light source member providing an extended, polarized light beam is directed through a transparent substrate and undergoes total internal reflection at the surface of the substrate by a single reflection within the TIR member. The reflected light is detected by a polarization-sensitive, two-dimensional array detector. The changes of the local polarization state in the beam's cross-section caused by the total internal reflection are employed to obtain information about the presence and composition in an array of substances on the substrate surface for each point of the surface. Total internal reflection is described in; M. Born, et al., "Principles of Optics", $6^{th}$ ed., pp 47–51, Pergamon Press, Oxford, 1991. In accordance with one aspect of the invention, the light generating element within the light source member is a quasi-monochromatic light source of moderate bandwidth. In a preferred embodiment, the light generating element within the light source member is an LED of moderate bandwidth. The light from the light source member is directed through an internal reflection member to reflect off a specimen. The total internal reflection at any point within the cross-section of the light beam causes a phase shift between the light component polarized in the plane of incidence and the component polarized perpendicular to the plane of incidence. The reflected light is detected by a polarization-sensitive, two dimensional array detector and the signal from this detector is then processed in a computer to provide two-dimensional information about substances on the surface of the specimen. Spatially distributed changes in polarization state in the cross-section of the reflected beam are indicative of the substances in the specimen in the location in the specimen array corresponding to a position in the detector. The apparatus and method is especially adapted for imaging material in an aqueous solution. It is furthermore particularly suited for detecting attachment and detachment of analytes to a two-dimensional biomolecular array positioned on the total internal reflection member as part of a biosensor system. In various applications a plurality of discrete specimen spots are presented in an array, where the method and apparatus will image the array so as to distinguish each of the discrete specimen spots by an image which represents the change in polarization state within each of the discrete specimen spots. Fluorescence or molecular tagging is not necessary nor practical for use in this invention.

BRIEF DESCRIPTION OF DRAWINGS

FIG. 1 is a block diagram of the invention.

FIG. 3 is a block diagram of alternative portions of the invention.

FIG. 4 is a block diagram of alternative portions of the invention.

FIG. 5 is a block diagram of alternative portions of the invention.

DETAILED DESCRIPTION

Figure 2:
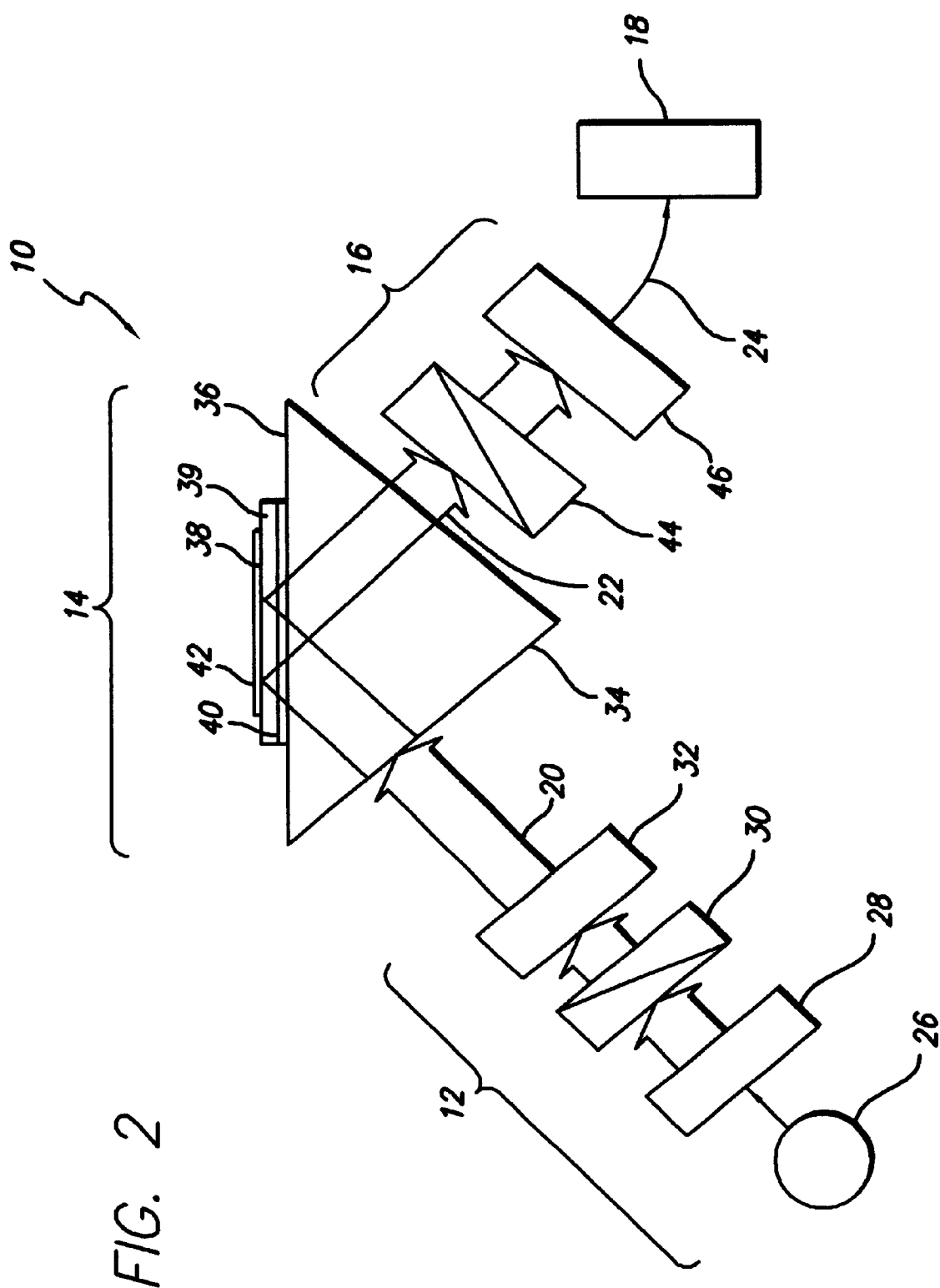
FIG. 2 is a block diagram of an embodiment of the invention.

The invention comprises a method and apparatus for analyzing a two-dimensional arrangement of chemical substances with an imaging technique. A polarized light source of known polarization state is directed into a total internal reflection member (TIR member) configured for a single reflection at a total internal reflection surface (TIR surface) and then exiting the TIR member. In the context of this document, superposition of reflections as encountered at a layered optical structure where the layer thicknesses are smaller than the coherence length of the illuminating light is referred to as a single reflection. The chemical specimen is in place above the TIR surface in the evanescent field of the reflected light beam. After reflection, the beam is passed to a polarization-sensitive two-dimensional detector such as a polarizer and a camera. The beam's content can then be processed to determine the change in polarization state, locally in the two-dimensional cross-section of the beam. This provides a spatially distributed map of change of polarization state in the specimen. A variety of techniques is available to determine the change in polarization such as measuring the deviation from a null condition or by comparing the input polarization state to the output polarization state.

The refractive index composition of the materials within the evanescent field determines the change in the polarization state of the beam due to the reflection at the TIR surface. A two-dimensional variation of this composition within the TIR surface is associated with a respective variation of the polarization state spatially distributed across the cross-section of the reflected light beam.

In one application, the chemical specimen forms a two-dimensional array of molecules (here referred to as receptors) with specific affinities towards respective other molecules (here referred to a ligands). In this application, the invention is utilized to indicate the presence or absence of binding between ligands and receptors on the array. Such arrays commonly consist of a plurality of discrete specimen spots. The present method and apparatus will image the array so as to distinguish each of the discrete specimen spots represented by the local change in polarization state in the cross-section of the reflected beam.

Subject to limitations in resolving power of the detector, the invention permits measurement of thickness and/or refractive index composition of the specimen under investigation with a very high resolution, in the sub angstrom range, spatially resolved over an entire area. The invention is particularly useful in applications where the specimen is in an aqueous solution. In a particular application, the present invention is used to determine the presence of biological agents in a solution such as in immunosensor applications by measuring their attachment to antibodies on the TIR surface in the evanescent field. In another application, the present invention is used to determine the presence and structure of nucleic acid sequences in a solution by measuring their attachment to other nucleic acid sequences on the TIR surface in the evanescent field. Described in more detail below are different embodiments of the invention.

Referring to FIGS. 1 and 2, an apparatus and method is illustrated which implements one embodiment of the invention. As shown in FIG. 1, the apparatus 10 can be conveniently described as consisting of three general portions. Portion 12 is a polarized light source assembly, portion 14 is a total internal reflection assembly and portion 16 is a polarization-sensitive two-dimensional array detector assembly. Data from the detector assembly 16 is sent by an electric signal 24 to processor 18 such as a specially programmed computer and user access system such as a printout or image display. Data can be presented as an image, a data table, or in other forms. The polarized light source assembly 12 passes polarized light of known polarization state (which may be varied or varying) 20 to the total internal reflection assembly 14 and the reflected light 22 having a changed polarization state passes to the detector assembly 16, where it is recorded spatially over the cross-section of the beam. The recorded data is sent to the processor 18 where the change of polarization state is determined to provide a spatially resolved map of changes in polarization state. Where the specimens are presented as an array of discrete spots, each spot will be imaged for its change in polarization state within the spot area.

FIG. 2 shows a more detailed preferred embodiment. The polarized light source assembly 12 has a light source 26, a beam forming member 28 (if the nature of the light source is such as to make beam forming useful or necessary) a polarizer 30 and an optical retarder 32. The total internal light reflection assembly 14 has a an optical element 34 which has an optical surface 36. Also shown is a specimen slide 38 on the optical surface 36, and between them an index matching substance 40. Because of the index matching a total internal reflection surface (TIR surface) is defined as the upper surface 39 of the specimen slide 38. A specimen 42 is on the total internal reflection surface 39 of the slide 38. The optical element 34 is a prism configured along with the index matched slide 38 in relationship to the incoming light beam 20, and the exiting light beam 22 such that the beam reflects only a single time at the TIR surface 39 and then exits the prism. If the specimen is placed directly on the optical surface 36, then the optical surface 36 would be the TIR surface. But this is not the usual application as the specimen (such as a biochip) is usually prepared more conveniently on a specimen slide 38 and placed in the apparatus. In any event, however constructed, there is an optical structure having a TIR surface and the beam reflects only a single time at the TIR surface between entering and leaving the optical structure. In other words, there is a TIR surface in optical contact with the specimen, such that the evanescent field associated with the total internal reflection interacts with the specimen, and there is only a single reflection at that TIR surface.

The post reflection detector assembly 16 has a polarizer 44, and a two-dimensional array detector 46, preferably a camera of the CCD type. The processor 18 is a specially programmed computer and output means for processing the imagery into a representation of film thickness variations spatially resolved over the cross-section of the area imaged. The imaging is acquired by detecting changes spatially distributed in the local polarization state in the beam's cross-section caused by the total internal reflection. This provides information about the presence and composition in the array of substances on the substrate surface for each resolvable point on the surface. Different polarization state changes are included in the cross-section of the reflected beam indicative of the substances on the specimen in the location in the specimen array corresponding to a position in the detector. The processor 18 receives the data as an electrical signal 24 and characterizes the change of polarization state spatially over the two-dimensional array. In the processor 18, the analysis and processing is done in one embodiment by comparing the known polarization state of the incoming light from the light processing assembly 12 with the changed polarization state of the reflected light 22, spatially resolved two-dimensionally within the beam which provides a map of spatially distributed points or spots in the specimen array. The polarization shift is then analyzed by the processor 18 to provide information of the presence and properties of elements in the chemical specimen. Other known techniques, such as null processing can be used to determine the change in polarization state.

Alternatively, the light source member 26 may be an LED, an SLD (Super Luminescent Diode), an incandescent light source, or a laser. If an LED or SLD is used, the set-up shown in FIG. 2 is appropriate, where the beam forming member 28 is a collimator. If an incandescent light source is used, an optical filter is also used.

In one embodiment, the light source 26 for the apparatus is a quasi-monochromatic light source of moderate bandwidth. In accordance with the invention the light source 26 is preferably an LED of moderate bandwidth. Preferably the bandwidth is a full width half maximum wavelength in the range of about 10 nm–50 nm, and more preferably a full width half maximum wavelength in the range of about 30 nm–50 nm.

Referring to the optical retarder 32 as shown in FIG. 2, in an alternative embodiment, the optical retarder could be placed instead in the exiting beam path 22 before the polarizer 44.

Referring to FIG. 3, an alternative embodiment is shown. When the light source is a laser 50, a moving diffuser 52 is adapted to produce speckle offsetting fluctuation of the minima and maxima in the speckle pattern caused by the laser. The moving diffuser 52 is attached to a mechanical actuator 54 which is preferably a motor and servo-apparatus for providing the speckle offsetting fluctuations. The beam 20 then proceeds through the beam forming element 28, the polarizer 30 and the optical retarder 32, exiting the light source assembly 20.

The polarizer 30 employs a polarizer of selected known polarization state. The polarizer 30 may be of the type having a mechanical actuator driven by a motor control signal so as to enable varying and selecting the polarization state of the light beam 20.

As mentioned above, the total internal reflection optical element 34 either alone or in combination with an index matched slide may be arranged for use with a specimen in various ways to define a total internal reflection assembly so long as the specimen is in the evanescent field of the reflected beam 20, 22.

As noted above, the specimen 42 could be set directly on the optical surface 36 in which case the optical surface 36 would be the TIR surface but this is inconvenient and repeated use is likely to degrade the optical quality of the optical surface 36, and therefore, consistent with common practice in which a biochip or other chemical assay specimen is provided, a specimen slide 38 or other supporting apparatus is employed. It is common in a biochip to provide an array of discrete specimen spots supported on a structure for obtaining analysis of each spot. The term total internal reflection optical element refers to known optical elements alone or in combination with other elements which provide the phenomenon known as total internal reflection. FIG. 2 shows use of a prism combined with a slide 38, being index matched so that there is a TIR surface 39.

FIG. 4 shows an alternative optical arrangement in which a flat optical member 56 having an upper surface 58 is surmounted by a specimen slide 60 and an index matching substance 62 on which is a specimen 64. The TIR surface 66 is the top of the slide 60. The beam 20 enters the assembly, is refracted as it enters, and leaves the optical member 56 after a single reflection at the TIR surface 66 as beam 22. Other mechanisms for providing total internal reflection and an evanescent field can be employed in practicing this invention as long as only a single reflection occurs at the TIR surface upon which the specimen is placed so as to be in the evanescent field associated with the reflection.

As seen in FIG. 5, the post-reflection processing arrangement 16 through which the beam 22 passes, can alternatively, consist of a polarizer member 70, a beam forming member 72 and a two-dimensional array detector 74.

The method and apparatus can be used in combination with biochips of the type having discrete specimen spots or a micro-titer plate containing an array of discrete spots or locations for analysis, where the detected change in polarization state is spatially related to the discrete locations in the reflected beam. Therefore, as used herein the slide and specimen refers to any type of chemical or biological array which is desired to be examined.

The foregoing described apparatus and methods are especially beneficial for imaging materials in an aqueous medium.

Although particular embodiments of the invention have been described and illustrated herein, it is recognized that modifications and variations may readily occur to those skilled in the art, and consequently it is intended that the claims be interpreted to cover such modifications and equivalents.

What is claimed is:

1. An imaging apparatus for imaging a specimen array within the evanescent field present upon reflection of a beam of light at a TIR surface comprising;
   a polarized light source member emitting a polarized, extended beam of light;
   a TIR structure having a TIR surface, the light from said polarized light source member being reflected only a single time by the TIR surface, the specimen being within the evanescent field associated with the total internal reflection at the TIR surface said specimen causing spatially distributed polarization changes in the beam's cross-section; and
   a polarization-sensitive, two-dimensional array detector, said detector resolving the light beam reflected from the TIR surface as an image of the spatially distributed polarization changes caused by the specimen.

2. Apparatus as in claim 1 wherein said polarized light source member comprises a quasi-monochromatic light source of moderate bandwidth.

3. Apparatus as in claim 2 wherein said quasi-monochromatic light source of moderate bandwidth is a light-emitting diode (LED).

4. Apparatus as in claim 2 wherein said quasi-monochromatic light source of moderate bandwidth is a superluminescent diode (SLD).

5. Apparatus as in claim 2 wherein said quasi-monochromatic light source of moderate bandwidth has an optical bandwidth with a full width half maximum between 5 nm and 60 nm.

6. Apparatus as in claim 2 wherein said quasi-monochromatic light source of moderate bandwidth comprises an incandescent source and an optical filter, the light emitted from said light source passing through said filter, said filter limiting the wavelengths of the light transmitted through said optical filter such as to constitute quasi-monochomatic light of moderate bandwidth.

7. Apparatus as in claim 1 wherein said polarized light source member comprises a laser emitting substantially coherent light, and further comprising an optical diffuser mechanically attached to a mechanical actuator, the light emitted from said laser passing through said diffuser, said diffuser being moved with respect to said laser by said actuator, the movement of said diffuser with respect to said laser creating fluctuations in the speckle pattern of light detected by said detector, said fluctuations being adapted to remove speckle effects from the light detected by said detector.

8. Apparatus as in claim 7, wherein said mechanical actuator is a motor rotating said optical diffuser.

9. Apparatus as in claim 1, wherein said polarized light source member comprises a beam forming system, said beam forming system causing the light emerging from said polarized light source member to be collimated.

10. Apparatus as in claim 1, wherein said polarized light source comprises an optical polarizer.

11. Apparatus as in claim 1 wherein said polarized light source member comprises an optical retarder, said retarder introducing an optical phase shift between two orthogonal components of light passing through said retarder.

12. Apparatus as in claim 11, wherein said optical retarder is set up to be controllably rotated by a motor.

13. Apparatus as in claim 11, wherein said optical retarder is set up to change its retardance according to an externally introduced physical parameter.

14. Apparatus as in claim 1, wherein said TIR structure comprises an optical prism.

15. Apparatus as in claim 14, wherein the light from said polarized light source member is directed to enter said prism along an axis perpendicular to one of the sides of said prism.

16. Apparatus as in claim 14, wherein the light reflected from said TIR surface exits said prism along an axis perpendicular to one of the sides of said prism.

17. Apparatus as in claim 1, wherein said specimen array comprises a two dimensional array of multiple fields comprising biomolecular substances.

18. Apparatus as in claim 17, wherein said biomolecular substances are proteins.

19. Apparatus as in claim 17, wherein said biomolecular substances are peptides.

20. Apparatus as in claim 17, wherein said biomolecular substances are polynucleotide sequences.

21. Apparatus as in claim 1, wherein said polarization-sensitive, two-dimensional array detector comprises an optical polarizer.

22. Apparatus as in claim 21, wherein said polarizer is set up to be controllably rotated by a motor.

23. Apparatus as in claim 1, wherein said polarization-sensitive, two-dimensional array detector comprises a two-dimensional CCD array.

24. Apparatus as in claim 1, wherein said polarization-sensitive, two-dimensional array detector comprises a two-dimensional photodiode array.

25. Apparatus as in claim 1, further comprising a signal processing member, said signal processing member being connected to said polarization-sensitive, two-dimensional array detector, said signal processing member processing the signal from said polarization-sensitive, two-dimensional array detector to obtain a two-dimensional representation of the optical phase shifts occurring in the specimen.

26. A method of imaging a chemical specimen array comprising;

passing an extended polarized light beam into a TIR structure for reflection at a TIR surface of the TIR structure and exiting after a single reflection at said TIR surface;

a specimen being in the evanescent field of the reflected light beam;

detecting the spatially distributed change in polarization state caused by the array; and processing the spatially distributed change in polarization state information detected to provide an image of the specimen array.

27. The method of claim 26 wherein said specimen array comprises a plurality of discrete specimen spots and said image is provided for each of said discrete specimen spots.

28. A method of characterizing a two-dimensionally distributed chemical specimen array in the evanescent field associated with total internal reflection of a beam comprising;

directing an extended beam of light of known polarization state at a total internal reflection surface, the beam undergoing a single total internal reflection at the total internal reflection surface;

determining the spatially distributed change in the beam's polarization state caused by the chemical specimen array in the evanescent field; and processing the spatially distributed change in polarization state information detected to provide an image of the specimen array.

29. The method of claim 28 further comprising using the spatially distributed change in the beam's polarization state, determining two-dimensionally distributed presence or properties or both of constituents of the chemical specimen array.

30. The method of claim 29 wherein the chemical specimen array is in a micro-titer plate comprising;

resolving the spatially distributed polarization changes in the light beam for matching positions in the micro-titer plate; and analyzing the polarization changes to determine desired characteristics in each position.

31. The method of claim 29 wherein the chemical specimen array is a series of discrete specimen spots; and the method comprises analyzing the polarization state changes to determine the binding characteristics of each discrete specimen spot in the array.

32. The method of claim 28 wherein a chemical specimen array having no molecular tagging is placed with the evanescent field associated with the beam.

\* \* \* \* \*

UNITED STATES PATENT AND TRADEMARK OFFICE
CERTIFICATE OF CORRECTION

PATENT NO. : 6,594,011 B1
DATED : July 15, 2003
INVENTOR(S) : Lothar U. Kempen

It is certified that error appears in the above-identified patent and that said Letters Patent is hereby corrected as shown below:

Column 1,
Line 3, add:

-- GOVERNMENT LICENSE RIGHTS

This invention was made with Government support under contract number DTRA01-99-P-0018 awarded by the Defense Threat Reduction Agency. The Government has certain rights in the invention. --.

Signed and Sealed this

Twenty-first Day of February, 2006

JON W. DUDAS
*Director of the United States Patent and Trademark Office*